United States Patent
Mirza et al.

(10) Patent No.: US 7,041,115 B2
(45) Date of Patent: May 9, 2006

(54) ENDOSCOPIC SURGICAL PROCEDURE

(75) Inventors: M. Ather Mirza, St. James, NY (US);
Amol Saxena, Palo Alto, CA (US);
Romi Mirza, St. James, NY (US)

(73) Assignee: A.M. Surgical, Inc., Smithtown, NY (US)

( * ) Notice: Subject to any disclaimer, the term of this patent is extended or adjusted under 35 U.S.C. 154(b) by 549 days.

(21) Appl. No.: 10/298,914

(22) Filed: Nov. 18, 2002

(65) Prior Publication Data

US 2004/0098005 A1    May 20, 2004

(51) Int. Cl.
*A61B 17/32* (2006.01)
(52) U.S. Cl. .................................... 606/170; 606/172
(58) Field of Classification Search ............... 606/170, 606/171, 172, 174, 180, 185; 604/164.01, 604/264
See application file for complete search history.

(56) References Cited

U.S. PATENT DOCUMENTS 5,366,465 A * 11/1994 Mirza ..................... 606/170
5,578,051 A * 11/1996 Mirza ..................... 606/170
5,968,061 A * 10/1999 Mirza ..................... 606/170

* cited by examiner

*Primary Examiner*—Kevin T. Truong
(74) *Attorney, Agent, or Firm*—Scully, Scott, Murphy & Presser

(57) ABSTRACT

An endoscopic surgical procedure on a patient, and more particularly, a novel and unique endoscopic surgical procedure known as an endoscopic gastrocnemius tenotomy to relieve posterior heel cord contracture tending to cause foot and ankle deformities.

12 Claims, 5 Drawing Sheets

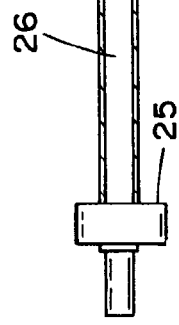
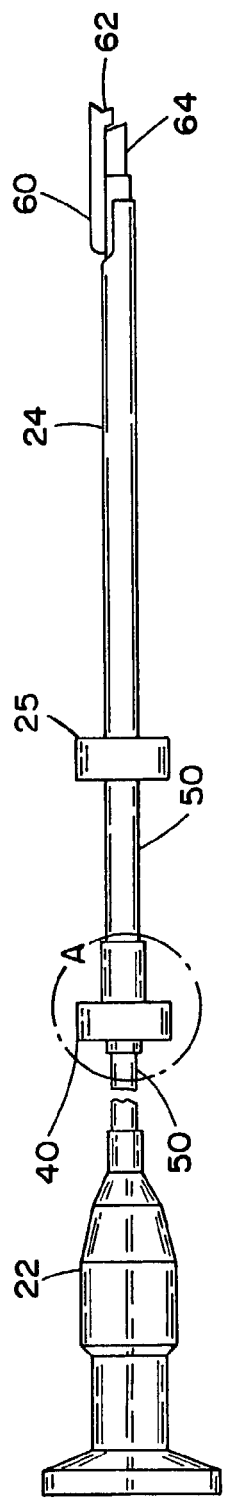
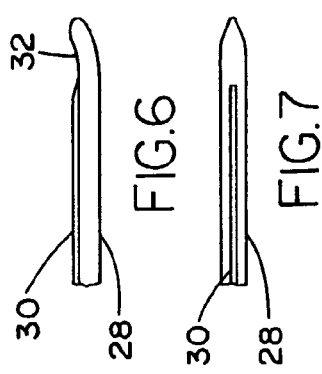
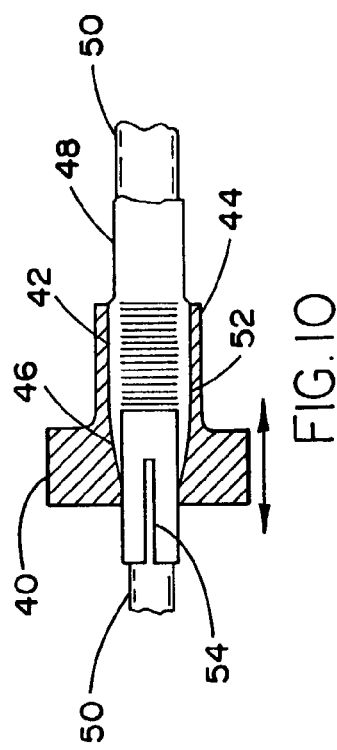

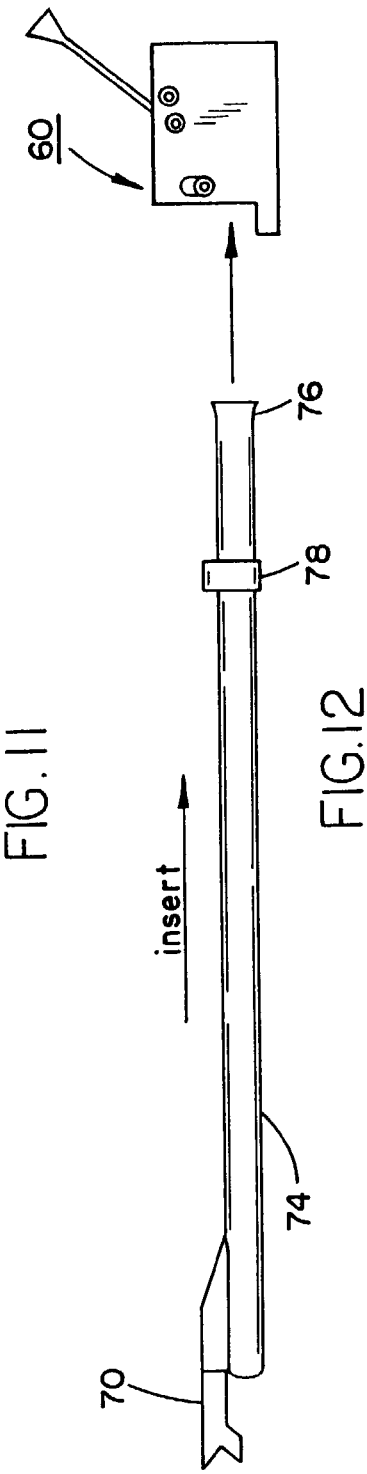
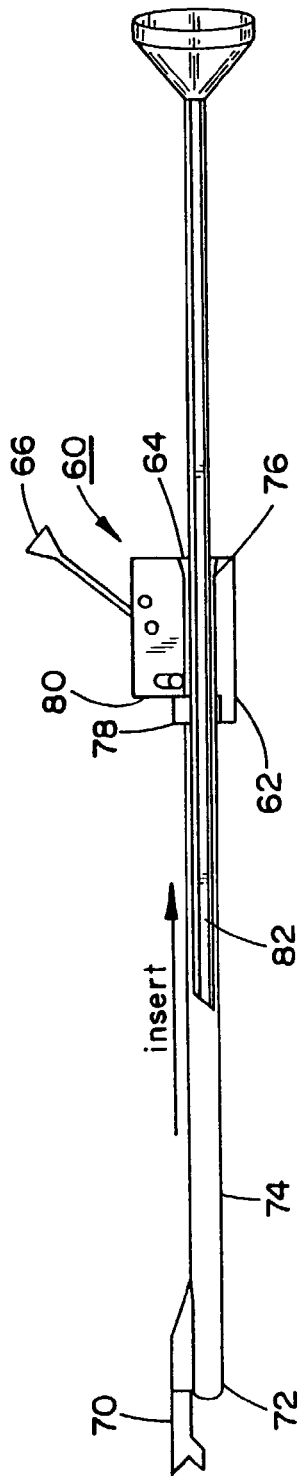

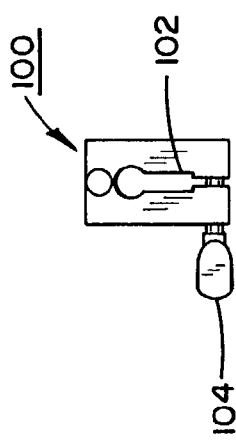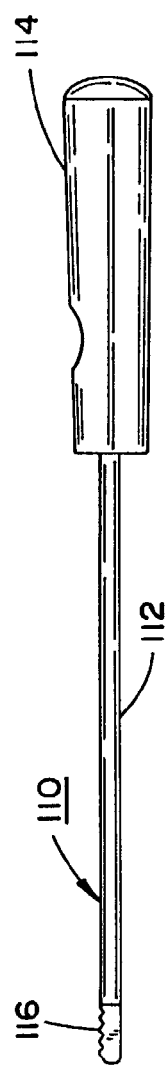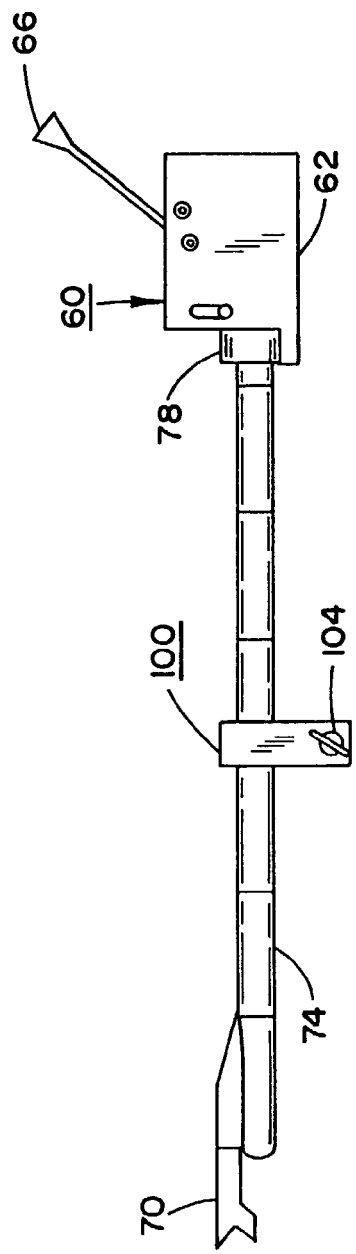

ENDOSCOPIC SURGICAL PROCEDURE

BACKGROUND OF THE INVENTION

1. Field of the Invention

The present invention relates to an endoscopic surgical procedure on a patient, and more particularly, is directed to a novel and unique endoscopic surgical procedure known as an endoscopic gastrocnemius tenotomy. In particular the surgical procedure may be implemented by means of a unique endoscopic surgical instrument in the form of a slotted cannula incorporating a novel locking device for an endoscopic instrument and for the surgical cutting element, such as a knife blade or rasp; and selectively, a depth gauge including calibrating structure for measuring the length or depth of the intended surgical procedure. Also incorporated therein is a calibrating structure for the endoscopic knife; and a stop device for use with the endoscopic knife and/or the depth gauge, and which is adapted to be employed in the implementation of the foregoing method of endoscopically effecting the above-referenced surgical procedure; this instruments being disclosed in Mirza U.S. Pat. No. 5,968,061; the disclosure of which is incorporated herein, and discussed hereinbelow in connection with the inventive endoscopic surgical procedure.

In particular, although initially described herein as being directed to the above-mentioned aspect of implementing a specific endoscopic surgical procedure, numerous other surgical procedures may be readily implemented employing the Mirza endoscopic surgical instrument, as mentioned hereinbelow.

Basically, improved endoscopic surgical procedures and endoscopic instruments are disclosed and directed to the implementation of endoscopic carpal tunnel release and other diverse surgical applications; as set forth in Mirza U.S. Pat. No. 5,366,465, issued Nov. 22, 1994, and U.S. Pat. No. 5,578,051, issued Nov. 26, 1996, and U.S. Pat. No. 5,968,061 issued Oct. 19, 1999 the disclosures of which are incorporated herein by reference.

Among more recent developments and advances in such surgical procedures, arthroscopic surgery employing the use of endoscopic devices has found widespread application, in that in comparison with earlier customary surgical methods, any incisions necessary for such endoscopic/arthroscopic surgical procedures have been considerably reduced in size, thereby alleviating potential postoperative complications and pain encountered by the patient, while reducing any scarring to cosmetically desirable levels. Among various types of surgical procedures, techniques involving approaches by means of arthroscopic and endoscopic systems to carpal tunnel surgery have been acknowledged as being superior in providing significant advances over earlier so-called open surgical procedures necessitating large incisions. Such endoscopic surgical procedures have found widespread acceptance in effectuating carpal tunnel release for the purpose of alleviating the symptoms in a patient caused by carpal tunnel syndrome, also referred to as tardy median nerve palsy, normally caused by the compression of the median nerve within the carpal tunnel.

More recently, consideration has been given towards extending the scope of the endoscopic surgical procedure to other aspects such as plantar fascia release associated with heel spur syndrome in which a patient encounters severe pain at the bottom of the foot. This aspect, which is caused by the dense fibrous band of tissue which is known as the plantar fascia, is that a disorder of the foot, such as a structural misalignment, can cause an inflammation and result in intense pain in the foot. Although in many instances therapy may remedy the problems which are encountered, at times surgery is necessary in order to alleviate the problems.

Among these problems, posterior heel cord contracture (ankle equines) has been implicated in many types of foot and ankle deformities. Lengthening of the Achilles tendon and the associated gastrocnemius-soleus complex has been advocated in reducing these equines deformities. This can be done as an open or a percutaneous procedure. The open procedures tend to have unappealing cosmesis and greater risk of wound complications. Percutaneous procedures do not allow for direct visualization. Furthermore, the functionality of posterior lengthening procedures has not been fully assessed. Over-lengthening can be disastrous, especially for patients who need to be able to stand on their toes. For purposes of illustration, the invention is described with regard to the implementation of an endoscopic surgical procedure employed in the treatment of posterior heel cord contracture.

2. Discussion of the Prior Art

Among numerous publications which describe recent advances in endoscopic surgical methods and instruments employed in connection therewith, there may be found the Agee carpal tunnel release system as disclosed in Agee, et al. U.S. Pat. Nos. 4,963,147 and 5,089,000, both of which disclose endoscopic surgical instruments and surgical procedures implemented therewith, which when applied to carpal tunnel release through an effective severing of the flexor retinaculum, or transverse carpal ligament, are adapted to provide relief to the patient.

Another surgical system and instrument providing for an advanced technique over Agee, et al., which is particularly adapted for carpal tunnel release through the intermediary of an endoscopic surgical procedure is disclosed in Chow U.S. Pat. No. 5,029,573. However, in that instance, although setting forth a considerable advance over the methodology disclosed in the Agee, et al. U.S. patents, the surgical procedure employed by Chow requires the formation of two entry and exit portals or incisions, one in the wrist area and one in the palm, and the passage of an endoscopic medical instrument, such as an obturator through a considerable length beneath the subcutaneous areas of the palm of the patient.

Another method of endoscopic surgery and instrument for implementing surgery, particularly for the release of the carpal tunnel, are disclosed in Brown U.S. Pat. No. 5,323,765. Although Brown directs the endoscopic surgery towards alleviating the syndrome encountered with the carpal tunnel, as in the previously discussed publications, two separate incisions are required. Moreover, although Brown also briefly mentions the application of the surgery and instrument or apparatus to the treatment of the foot, particularly the plantar fascia, again there is no detailed explanation provided as to the method in which this is accomplished, and apparently this would also necessitate providing a plurality of separate incisions to implement the surgery.

More recently, as described in Mirza U.S. Pat. No. 5,366,465, the foregoing limitations and potential drawbacks which are encountered in the previously mentioned prior art publications have been improved upon through a novel method of implementing endoscopic surgical procedures, and a unique and inventive endoscopic surgical instrument developed for accomplishing this purpose, which has proven itself to be especially suited for, but not limited to, the effectuation of carpal tunnel release. In essence, the Mirza patent is directed to the severing of the flexor retinaculum or transverse carpal ligament through an endoscopic surgical procedure in which there is effected, by means of a uniportal or single incision, a palmar subligmentous endoscopic carpal tunnel release technique. This surgical procedure only requires the formation of a single and relatively small entry portal or incision in the palm proximate the distal side of the flexor retinaculum, thereby reducing any postoperative symptoms of the patient with only a cosmetically appealing scar formed on the palm, while eliminating the need for a second portal or incision proximate the wrist of the patient; and concurrently avoiding injury to the palmar arch and branches of the median nerve. Moreover, the endoscopic instrument employed in implementing the surgical method utilizes a cutting device which is mounted on a scope insertable through a cannula which has been initially inserted to extend beneath the flexor retinaculum from the distal side of the flexor retinaculum or transverse carpal ligament, upon the formation of a passage beneath the flexor retinaculum, after hyperextending of the hand, by the preceding insertion and manipulation of a curved dissector. Thereafter, the dissector is removed and the cannula and an obturator which is contained therein are inserted through the incision into the previously formed passage beneath the flexor retinaculum. The cannula of the surgical instrument has the obturator withdrawn therefrom, and in place of the latter, a scope is inserted into the cannula which enables unhindered and unobstructed visualization of the operating site and of the flexor retinaculum.

The scope is then withdrawn from the cannula, and the same scope or another scope with a cutting blade mounted at the leading end thereof inserted into and advanced through the cannula towards the flexor retinaculum. Severing of the latter is then effected by the cutting blade while affording an unhindered view of the operating site through the scope, thereby resultingly dramatically reducing or even completely eliminating the risk of any injury being sustained by tissue and nerves in the vicinity of the operating site; for example, such as the median nerve. This particular unhindered visualization of the operating site also enables the surgeon to exercise an improved degree of control over the possibly single-handed manipulation of the endoscopic instrument and cutting blade.

The cannula of the endoscopic instrument, which contains the obturator which is initially employed to be advanced beneath the flexor retinaculum or transverse carpal ligament subsequent to withdrawal of the curved dissector, may be provided with lateral or sideways wing-like or flange-like protrusions of curvilinear configurations which, in conjunction with an upwardly curving tip of the obturator projecting forwardly of the leading end of the cannula, is adapted to displace any tissue, or such as the media nerve, out of the path of the obturator and cannula as is being advanced; in effect, through essentially a sideways or lateral "shoving" action, thereby preventing any potential damage to such displaced tissue and nerve during the subsequent cutting procedure by maintaining such tissue well out of the way. Moreover, the leading tip of the obturator by being curved slightly upwardly towards the lower surface of the flexor retinaculum is also adapted to remove or dislocate any possible tissue or fascia located close to the surface of the flexor retinaculum and to ensure that the cannula and, resultingly, the subsequently inserted cutting blade are located as closely as possible to the flexor retinaculum.

Although described hereinabove with regard to the effectuation of a carpal tunnel release, the inventive uniportal endoscopic surgical methods and instrument may be also be readily applied to other surgical procedures; for example, such as uniportal plantar fascia release, lateral release for patella realignment, release of the posterior and other compartments of the leg, and forearm fascia release for fascial compartment syndrome. To that effect, reference may be had to the disclosure of Mirza U.S. Pat. No. 5,578,051 which considerably expands the surgical field of applications of the previous Mirza patent and also incorporates additional features in the endoscopic surgical instrument.

The foregoing endoseopic surgical methods, particularly the uniportal surgical procedures and surgical instruments developed by the Mirza U.S. Pat. Nos. 5,366,465, 5,578,051 and 5,968,061, the disclosures of which are incorporated herein by reference, although providing considerable advantages over the current state of the art, are still further simplified by providing an improved composite slotted cannula and dissector of unitary or integral construction which eliminates a need for the provision of a separate dissector or a separate obturator, thereby reducing the number of surgical steps in the implementation of the various procedures. A particular aspect of eliminating the separate dissector and obturator heretofore utilized resides also in the composite cannula and dissector which forms the passageway towards the surgical site enabling an improved control during insertion thereof, and by reducing the surgical steps during the implementation of the procedure renders the entire operation less expensive and of shorter duration, so as to further minimize any potential discomfort to a patient.

SUMMARY OF THE INVENTION

Accordingly, the present invention is directed to a novel and unique method of implementing an endoscopic surgical procedure through a uniportal entry to an operating site by means of a novel endoscopic surgical instrument.

The present invention is further directed to an endoscopic surgical procedure or method of effecting an endoscopic gatrocnemius tenotomy intended to alleviate problems encountered in connection with posterior heel cord contracture leading to foot and ankle deformities.

Pursuant to another aspect of the invention, in lieu of a cutting knife being attached to the end of the sleeve which is adapted to be positioned over the endoscope and then inserted into the slotted cannula, there may be provided a suitable depth gauge for measuring the length of the insertion with the endoscopic knife. For this purpose, there may be also be provided a suitable stop device which is mountable on the sleeve for respectively the endoscopic cutting knife and the depth gauge, and which would also limit the insertion of the endoscopic device into the uniportal entry formed in the patient.

Pursuant to another aspect of the invention, the endoscopic element which is inserted into the slotted cannula and which has the knife instrument mounted thereon to perform the surgical procedure, as described in the aforementioned Mirza U.S. patents, may be optionally replaced by a rasp member or structure which is able to pull out a so-called "curtain" of tissue; for example, during a particular procedure employed to relieve carpal tunnel syndrome at the ulnar bursa where the latter attaches to the flexor retinaculum. The rasp element is adapted to scrape the undersurface of the flexor retinaculum and to remove tissue adhering thereto.

BRIEF DESCRIPTION OF THE DRAWINGS

Reference may now be made to the following detailed description of a procedure or method of implementing an endoscopic gastrocnemius tenotomy, preferably by employment of a endoscopic surgical instrument constructed pursuant to Mirza U.S. Pat. No. 5,968,061, taken in conjunction with the accompanying drawings; in which:

FIG. 6 illustrates a longitudinal side view of the leading end of an obturator adapted to be inserted into the slotted cannula of FIG. 2 or 4;

FIG. 7 illustrates a top view of the leading end of the obturator;

FIG. 8 illustrates a longitudinal side view of the endoscopic instrument, showing the scope and cutting device mounted on the latter inserted into the slotted cannula;

FIG. 9 illustrates a top view of the leading section of the endoscopic instrument shown in FIG. 8;

FIG. 10 illustrates, on a somewhat enlarged scale, a sectional view of the encircled portion A of the instrument of FIG. 8;

FIG. 11 illustrates a side view of the locking device;

FIG. 12 illustrates a tubular member mounting a surgical knife being inserted into the locking device;

FIGS. 13 and 14 illustrate the assembling of the components including an endoscope;

FIG. 17 is a sectional view taken along line 17—17 in FIG. 16;

FIG. 18 illustrates a rasp member adapted to scrape a curtain of tissue at an operating site; and FIG. 19 is a view similar to FIG. 16, showing the tubular member mounting a cutting blade instead of a depth gauge.

DETAILED DESCRIPTION OF A PREFERRED EMBODIMENT

Figure 1:
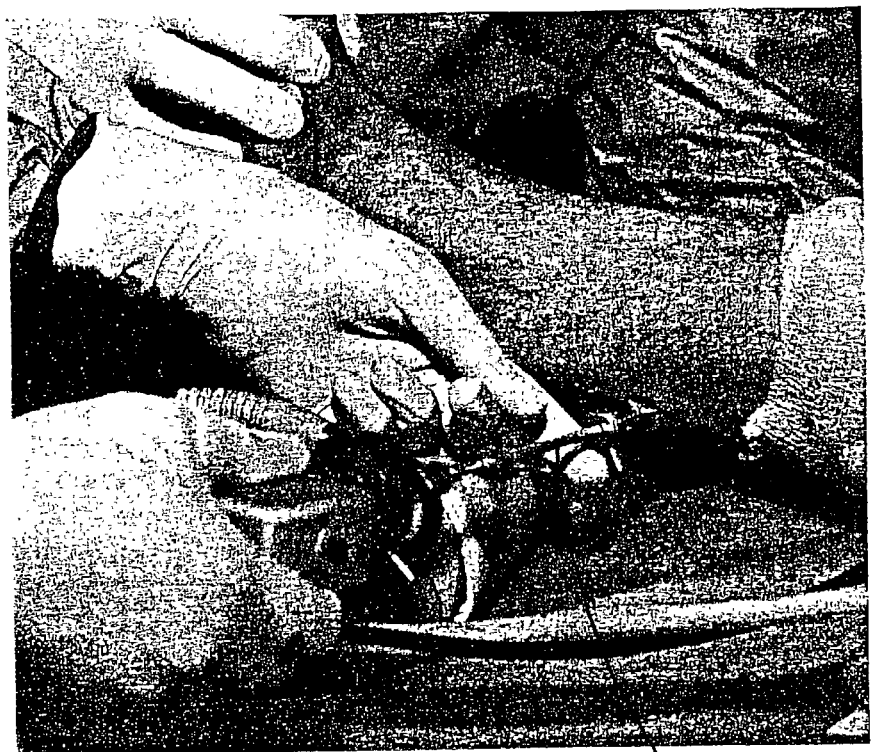
FIG. 1 illustrates a generally representative view of the foot of a patient during a surgical procedure for effecting a gastrocnemus tenotomy utilizing the endoscopic surgical instrument.

As shown in FIG. 1 of the drawings, the endoscopic instrument 10 which is to be utilized for effectuating the surgical procedure; in effect, the endoscopic gastrocnemius tenotomy, is shown in the operative position thereof inserted through an incision into the foot of a patient. Although shown in the Mirza U.S. Pat. No. 5,968,061, the instrument is described in detail herein for purposes of clarity in connection with the inventive surgical procedure.

Figures 2, 3:
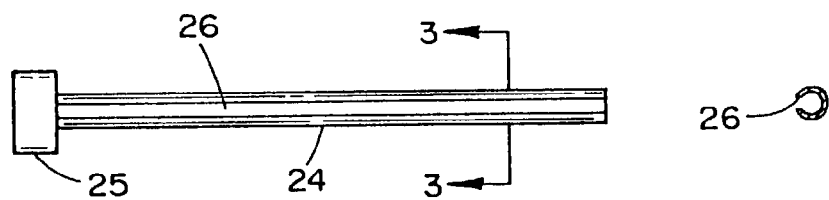
FIG. 2 illustrates a longitudinal top view of a slotted cannula of the endoscopic surgical instrument.
FIG. 3 illustrates a sectional view taken along line 3—3 in FIG. 2.

Referring to FIGS. 2 through 10, the endoscopic surgical instrument 10 comprises an arthroscope 22 which includes a cannula 24 having a through extending longitudinal slot 26 formed therein, and a knob or flange-like member 25 at one end thereof, as shown specifically in FIGS. 2 and 3 of the drawing.

The knob or member 25, as shown in the drawings, has a central aperture which is sized to facilitate passage therethrough with sufficient clearance of any obturator, scope and cutting element which is to be inserted into and withdrawn from the cannula 24 and which projects through longitudinal slot 26, as described in detail hereinbelow.

An obturator 28, as in FIGS. 6 and 7, is adapted to be slidably received within the cannula, and presents a smooth outer surface through the intermediary of an axial, upstanding rib portion 30 which is engageable in close conformance within the longitudinal slot of the cannula upon insertion therein. The leading end of the obturator 28 is a tapered tip portion 32 which is bent upwardly in a direction towards the longitudinal rib to impart to the tip a somewhat upward curvature for a purpose to be described hereinbelow in more extensive detail. The leading end of the cannula may also be configured to form an integral obturator and dissector thereby eliminating separate components.

Figures 4, 5:
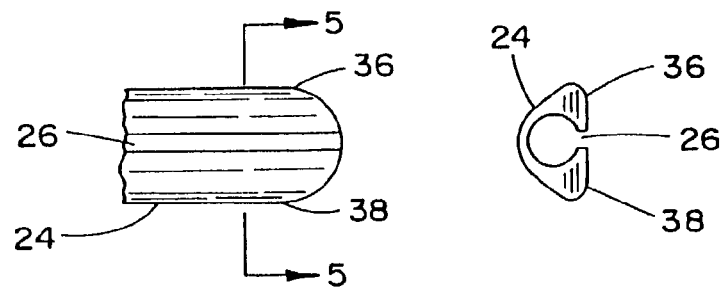
FIG. 4 illustrates a top view of the leading end portion of a modified slotted cannula.
FIG. 5 illustrates a sectional view taken along line 5—5 in FIG. 4.

Although the cannula 24, as shown in FIGS. 2 and 3, is illustrated as being circular in crosssectional configuration along its external surface, pursuant to a modified embodiment, as shown in FIGS. 4 and 5, at opposite sides of the longitudinal slot 26, the outer surface of the cannula 24 may be equipped with integrally formed outwardly extending curvilinear flange portions 36 and 38 so as to essentially form so-called wings or fins, as described further on hereinbelow. These fin-like wings or flange portions 36 and 38 are integrally formed with the cannula and are also curved so that upon insertion of the obturator into the cannula, the tip end of the obturator essentially forms a smooth curvature at its juncture with the flanges 36 and 38.

As shown more specifically in FIGS. 8 through 10, the endoscopic instrument 10 is illustrated in its condition for cutting through the flexor retinaculum to effectuate carpal tunnel or ligament release.

Hereby, the arthroscope 22 includes a suitable knurled knob 40 having an internal threaded portion 42 in a cylindrical extension 44 and a tapered bore 46 for receiving a tubular knife or cutting blade holder 48. The blade or knife holder 48 is adapted to receive a scope 50 of cylindrical configuration extending therethrough and lock the latter within the blade holder by simply axially displacing the knurled nut 40 through threaded interengagement between the internal thread 42 of the nut and an external thread 52 on the blade holder.

This will cause the tapered bore 46 of nut 40 to either compress the slotted portion 54 of the blade holder to clampingly engage the scope 50 or to loosen it so as to enable axial adjustment thereof relative to the blade holder.

A scope in the form of a rod member, in the absence of a blade holder, and which is connected to a video scanner (not shown) is adapted to be inserted through the cannula for effective visualization of the operative site.

In order to improve upon the structure of the endoscopic surgical instruments as disclosed in the applicants earlier U.S. Pat. Nos. 5,366,465 and 5,578,051, the disclosures of which are incorporated herein by reference, in accordance with a specific feature there is provided a unique locking device for the attachment of either a cutting instrument or a depth gauge to an endoscopic rod element, whereby these components are adapted to be inserted into the slotted cannula.

As illustrated in the drawing FIGS. 11 through 14, the locking device 60 includes a rectangular housing structure 62, having a longitudinal through bore 64 for receiving a tubular element supporting a gauge or cutting blade and for receiving a rod-like endoscope. A pivotable lever 66 mounted on the housing structure 62 is adapted to be swung between an opened position to a locked position so as to impart a clamping action to a tubular element extending through bore 64 by means of a camming structure, as explained hereinbelow.

Pursuant to one aspect, a cutting instrument, such as a surgical knife 70, which may be disposable, as shown in drawing FIG. 12, is mounted at the leading end 72 of an elongate hollow tubular member 74 towards the opposite end of which the latter includes a hub portion 76 and a ring 78 spaced at a short distance therefrom, which forms a spacer defining the length of the tubular member 74 extending towards the knife blade 70, or any cutting or rasp instrument for removing tissue, such as a "curtain" of tissue, which is provided instead of the knife blade 70.

Figure 14:
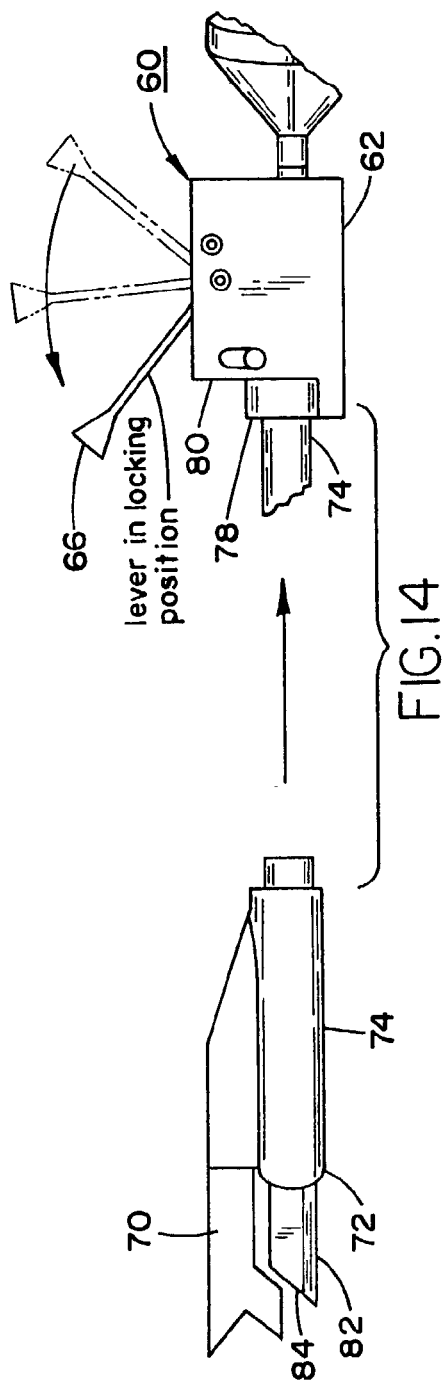

As shown in FIGS. 12 to 14, in diagrammatic sequence, the hub end portion 76 of the hollow tubular member mounting the cutting or rasp instrument or the knife 70 at the opposite end 72 is adapted to be positioned within the bore 64 formed in the locking device 60, and is inserted therein to the extent such that the spacer 78 ring which is fastened to the tubular member 74 comes into contact with the leading or forward surface 80 of the locking device 70. At that point in time, the endoscope 82 is advanced through the hollow tubular member 74 which mounts the cutting instrument or knife 70, as shown in FIG. 13, and the leading end 84 of the endoscope 82 positioned closely to the cutting blade or instrument 70, similar to the arrangements described in the above-mentioned earlier Mirza, U.S. Pat. Nos. 5,366,465 and 5,578,051.

As shown in FIG. 14, as the endoscope 82 has its leading end 84 appropriately positioned in proximity relative to the knife or cutting instrument 70, the lever 66 is pivoted forwardly into the locking position, thereby causing the endoscope 82 to be clamped to the tubular member 74 mounting the cutting element or blade 70. This will then facilitate ready insertion of the resultingly locked together components into the slotted cannula.

Figure 15:
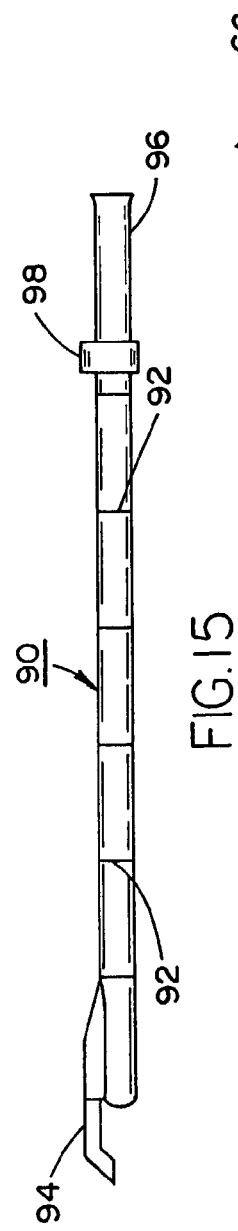
FIG. 15 illustrates the tubular member mounting a depth gauge.

The foregoing locking device 60 provides for a versatility not at all ascertainable in the technology, noting that the elongate tubular element 74 which mounts the knife or cutting element 70 at the leading end 72, may be calibrated along the length thereof so as to provide indication as to the depth to which the instrument is being introduced into the patient towards the surgical site. In this connection, in lieu of the tubular member mounting a knife or cutting element 70, prior to the use thereof with the endoscope 82, a tubular element 90 having calibrating markings 92 along the length thereof, which is similar to tubular element 74, may be equipped with a depth gauge 94 at the leading end thereof, as shown in FIG. 15, which, in a manner similar to the tubular member 74 mounting a knife or cutting element, is adapted to be inserted at the hub end 96 thereof into the locking device 60 until ring 98 contacts the locking device, with the endoscopic element inserted therein to provide illumination of the operating site, and the lever 66 being swung forwardly into the locking position.

Figure 16:
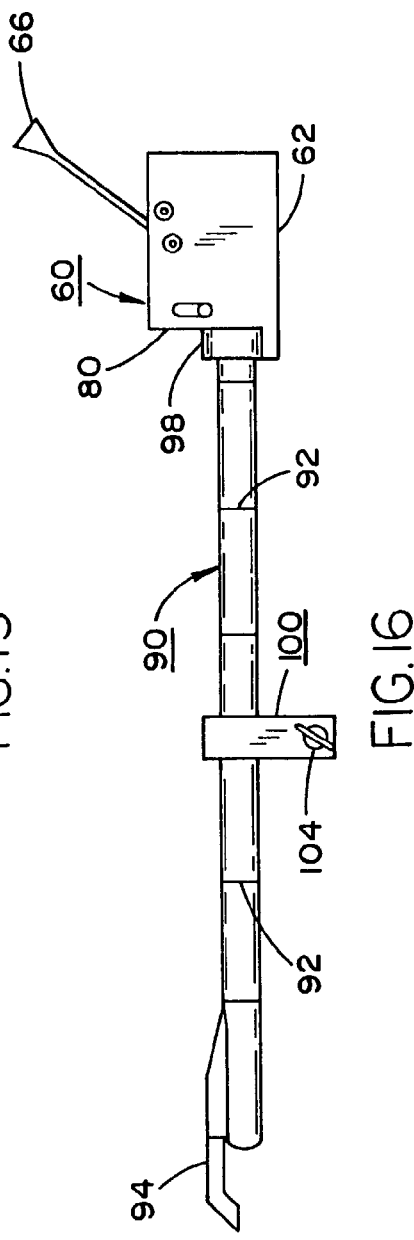
FIG. 16 illustrates the tubular member mounting the depth gauge connected to the locking device and having a stop device for limiting the extent of insertion into an incision formed in a patient.

Upon determination of the appropriate insertion depth to the surgical site by means of the tubular member 90 mounting the depth gauge 94, having the endoscope mounted therein, it is desirable to mount a stop device 100 in the form of a clamp member 102 on the tubular element 90 mounting the depth gauge 94, as shown in FIGS. 16 and 17, and tighten a clamping element 104, such as, for instance, a tightening screw, and which will provide information with regard to the cutting depth which is to be subsequently implemented, in that the stop device is positioned against or in proximity with the skin of the patient at the location of the incision, while the tubular element 90 and the endoscope therein are advanced within the cannula.

Upon withdrawing the tubular element 90 mounting the depth gauge 94 from the slotted cannula, a tubular element 74 mounting a knife or cutting element may be substituted therefore, as shown in the drawing FIGS. 12 to 14, and wherein the tubular member 74 or element mounting the knife or cutting instrument is similarly calibrated along its length. A stop device 100 is then fastened thereon at a location conforming with that of the stop device which was previously mounted on the calibrated tubular member 90 mounting the depth gauge 94. This will enable the precise determination of the depth to which the cutting instrument can be inserted through the cannula into the operating site, thereby preventing any injury due to any excessive penetration past the surgical site by the cutting instrument.

Furthermore, in lieu of the use of a knife blade being mounted on a tubular member 74, as the cutting element there may also be employed a unique rasp member 110 having a plurality of transverse cutting edges formed thereon, and which is adapted to scrape tissue at the operating site. The rasp member 110, as shown in FIG. 18, may be in the form of a solid rod element 112, which is insertable into the cannula, including a gripping end 114 and having the rasp elements 116 at the leading end thereof for advance towards the operating site. Alternatively, the rasp may comprise rasp elements mounted on a hollow tubular element similar of the type which supports the depth gauge 94 or knife 70, and is adapted to be fastened to the locking device 60 and with an endoscope passed therethrough, with the lever 66 of the locking device thereafter locking the components into mutually fixed positions.

DESCRIBED HEREINBELOW IS THE INVENTIVE ENDOSCOPIC GASTROCNEMIUS TENOTOMY PROCEDURE

A 1-cm vertical incision is made medially on the leg inferior to the medical gastrocnemius muscle belly. A clamp is used to bluntly dissect down the fascia. The plantaris tendon may need to be dissected away. A fascial elevator is used to separate the subcutaneous tissue (which contains the saphenous neurovascular structures) from the gastrocnemius fascia. The obturator/cannula 28,24 is inserted followed by the 4-mm endoscope 22. The neurovascular structures are completely protected in this manner. The fascia is well visualized and looks similar to endoscopic visualization of the plantar fascia. The endoscope is temporarily removed. A cannulated, camera-mounted knife 70, which only can cut what is in the cannula 24, is then carefully inserted vertically through the incision. Carefully rotating the knife 90° towards the fascia avoids potential damage to neurovascular structures.

The knife cuts as it is pushed through the cannula. The foot is dorsiflexed to aid in transection; however, entrance into the soleus muscle can result in hemorrhage, obscuring visualization. In younger patients, the gastrocnemius fascia is wider. Therefore the lateral fibers may need to be transected from a second portal laterally. The cannula can be pushed laterally from the medial incision so that a cut-down incision can be made. The cannula is re-inserted laterally, and a similar technique is used to cut the fibers from lateral to medial. Similar to an endoscopic plantar fasciotomy, which allows visualization of the first layer of plantar musculature after a successful release, the soleus muscle should be visualized after the tenotomy. Instrumentation is then removed, the wounds are irrigated, and skin closure is performed. Postoperatively, the foot is splinted according to the outer procedures performed. Otherwise, a below-knee cast boot is maintained for 3–4 weeks.

There is minimal morbidity and convalescence with this procedure. At this time, it is not expected that any patients have any neurovascular or wound compromise (an advantage for diabetics), and they would have gained at least 10° of dorsiflexion. More importantly, this procedure does not compromise propulsion, which is restored usually within 6–12 weeks. This procedure, in essence, is creating a "tennis leg" or medical gastrocnemius tear. Patients sustaining this injury usually are deemed able to return to athletic activity with proper rehabilitation.

Quite apparently, by only slightly modifying the lengths and diameters of the surgical endoscopic instrument, it is possible to customize, within the scope of the invention, the endoseopic surgical instrument so as to be adapted for other numerous endoscopic surgical procedures of the type described herein.

While there has been shown and described what is considered to a preferred embodiment of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A method of implementing a uniportal endoscopic surgical procedure to effectuate a gastrocnemius tenotomy for creating a medical gastrocnemius tear on the foot of a patient so as to relieve posterior heel cord contracture tending to cause foot and ankle deformations; comprising the steps of:

making an incision medially on the leg of said patient in a region inferior to the medical gastrocnemius muscle belly and exposing the fascia proximate said operative site to establish an entry portal; identifying and bluntly dividing the fascia, and separating the fascia from subeuteneous tissue from the gastrocnemius fascia to form a pathway;

inserting an elongate insertion member into a longitudinal bore of an elongate cannular guide member having open proximal and distal ends and an open slot extending along the length thereof communicating with said open ends, said elongate insertion member being slidably receivable within said cannular guide member and being configured so that at least portions thereof conform with said open distal end and said open slot of the guide member to form a smooth exterior surface in combination therewith;

introducing a leading end of the combination of said cannular guide member and the therein inserted insertion member into said entry portal and advancing said combination along said pathway a predetermined distance relative to said operative site;

withdrawing said insertion member while permitting said cannular guide member to remain in place at said operative site;

inserting endoscopic viewing means into said cannular guide member for direct visualization of said operative site and fascia and the positioning of said guide member relative to said site;

withdrawing said endoscopic viewing means from said cannular guide member, mounting a surgical instrument on further endoscopic viewing means proximate the leading end of said viewing means;

inserting said composite further endoscopic viewing means and surgical instrument into said cannular guide member such that the surgical instrument protrudes into the open slot in said cannular guide member, and advancing said composite endoscopic viewing means and surgical instrument so as to contact tissue at said operative site with said surgical instrument;

operatively engaging said tissue with said surgical instrument while advancing and rotating the latter under direct visualization through said further endoscopic viewing means to allow visualizing of the soleus muscle after the tenotomy;

withdrawing said composite further endoscopic viewing means and surgical instrument from said cannular guide member;

withdrawing said cannular guide member through said entry portal, irrigating the wound, and suturing said incision.

2. A method as claimed in claim 1, wherein the first-mentioned endoscopic viewing means is reinserted into said cannular guide member after withdrawing said composite further endoscopic viewing means and surgical instrument to enable inspection of the operating site; withdrawing said endoscopic viewing means from said cannular guide member and reinserting said elongate insertion member into the bore of said cannular guide member whereby said cannular guide member is withdrawn through said entry portal conjointly with said insertion member.

3. A method as claimed in claim 1, wherein said surgical instrument employs a cutting sequence severing tissue at said operative site.

4. A method as claimed in claim 3, wherein said cutting action is effective with a blade member having a leading cutting edge for severing tissue responsive to advancing said further endoscopic viewing means forwardly within said cannular guide member.

5. A method as claimed in claim 4, wherein said open slot in said cannular guide member has the opposite said edges thereof forming guide surfaces for said blade member inhibiting rotation of said blade about the longitudinal axis of said cannular guide member.

6. A method as claimed in claim 4, wherein the leading end of said further endoscopic viewing means includes an angled surface facing said blade member for directing illuminating light against the blade member and towards the region of the operating site proximate at least the cutting edge of said blade member.

7. A method as claimed in claim 1, wherein said insertion member comprises an obturator.

8. A method as claimed in claim 7, wherein said obturator has a tapered leading tip portion.

9. A method as claimed in claim 8, wherein said tapered leading tip portion of the obturator includes a curvature so as to angle the tip portion towards the plane of the cannular guide member possessing the open slot.

10. A method as claimed in claim 1, wherein adjustable limits are imposed in advancing said composite further viewing means and surgical instrument within said cannular guide member relative to said operative site.

11. A method as claimed in claim 3, wherein said surgical instrument is rotated about an angle of about 90° toward the fascia during said cutting sequence so as to avoid potentially damaging neurovascular structures in the patient.

12. A method as claimed in claim 1, wherein said incision comprises a 1-cm vertical incision.

* * * * *